US00PP36330P2

(12) United States Plant Patent
Jansen

(10) Patent No.: US PP36,330 P2
(45) Date of Patent: Dec. 17, 2024

(54) ***SCABIOSA* PLANT NAMED 'ScaMav01'**

(50) Latin Name: *Scabiosa caucasica*
Varietal Denomination: ScaMav01

(71) Applicant: Ben Jansen, Sint Maarten (NL)

(72) Inventor: Ben Jansen, Sint Maarten (NL)

(73) Assignee: Kwekerij Tunezo (NL)

( * ) Notice: Subject to any disclaimer, the term of this patent is extended or adjusted under 35 U.S.C. 154(b) by 0 days.

(21) Appl. No.: 18/659,634

(22) Filed: May 9, 2024

(51) Int. Cl.
*A01H 5/02* (2018.01)
*A01H 6/00* (2018.01)

(52) U.S. Cl.
USPC ..... Plt./478

(58) Field of Classification Search
USPC ..... Plt./478
See application file for complete search history.

*Primary Examiner* — Susan McCormick Ewoldt
(74) *Attorney, Agent, or Firm* — Cassandra Bright

(57) ABSTRACT

A new and distinct cultivar of *Scabiosa* plant named 'ScaMav01', characterized by very full, double inflorescences with a unique musky scent. Plants are easy to propagate and flower over a long period of time, Spring Summer and Autumn. Flowers are exceptionally large. *Scabiosa* is a popular genus for ornamental purposes, including container and landscape plants as well as cut flowers.

2 Drawing Sheets

Latin name of the genus and species: *Scabiosa caucasica.*
Variety denomination: 'ScaMav01'.

BACKGROUND OF THE INVENTION

The new *Scabiosa* cultivar is chance discovery by the inventor. The new cultivar was discovered as a spontaneous, naturally occurring whole plant mutation at a commercial nursery in Heemskerk, the Netherlands.

The parent variety is the unpatented variety *Scabiosa caucasica* 'Perfecta Blue'. The new cultivar was discovered in 2021.

Asexual reproduction of the new cultivar 'ScaMav01' was first performed by vegetative cuttings during 2021, in Heemskerk, the Netherlands. Subsequent propagation has shown that the unique features of this cultivar are stable and reproduced true to type in three successive generations. There have been no sales to date, and a CPVO application was made on May 11, 2023, application number 2023/1039 by the inventor.

SUMMARY OF THE INVENTION

The cultivar 'ScaMav01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ScaMav01'. These characteristics in combination distinguish 'ScaMav01' as a new and distinct *Scabiosa* cultivar:

1. Very full, double inflorescences.
2. Easy to propagate.
3. Unique musky scent to flower.
4. Long flowering period.
5. Large flowers.

PARENT COMPARISON

Plants of the new cultivar 'ScaMav01' are similar to plants of the parent variety, in most horticultural characteristics, however, plants of the new cultivar 'ScaMav01' differ in the following;

1. Plants of the new cultivar are easier to propagate than plants of the parent variety.
2. The new variety produces more flowers per inflorescence than the parent.
3. Inflorescences of the new cultivar are very full, double; inflorescences of the parent variety are single.

COMMERCIAL COMPARISON

Plants of the new cultivar 'ScaMav01' can be compared to the commercial variety *Scabiosa* 'Butterfly Blue', unpatented. These varieties are similar in most horticultural characteristics; however, 'ScaMav01' differs in the following:

1. Plants of the new variety are taller than plants of this comparator.
2. Flower stems of the new variety are stronger than flower stems of this comparator.
3. Flowers of the new variety are larger than flowers of this comparator.
4. The new variety produces more flowers per inflorescence than this comparator.

BRIEF DESCRIPTION OF THE PHOTOGRAPHS

Figure 1:
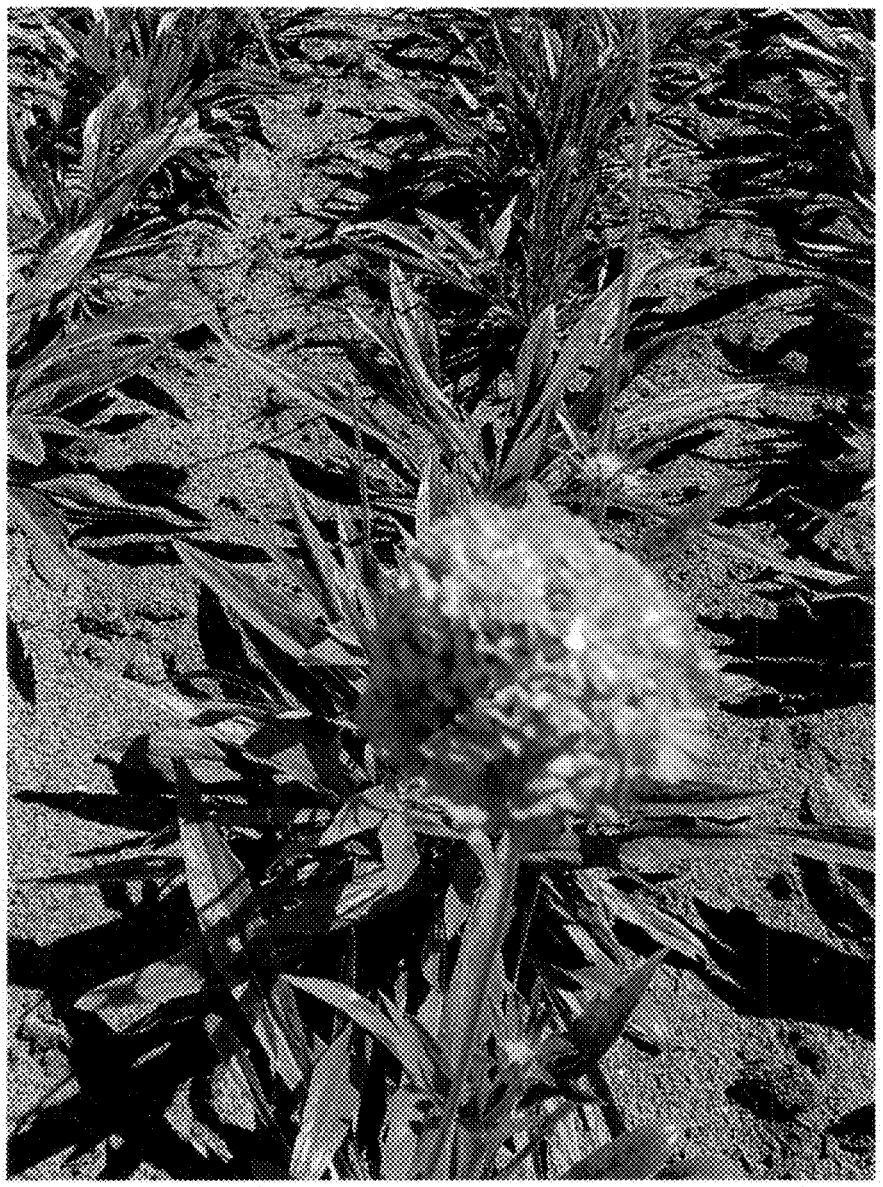

The accompanying photograph in FIG.1 illustrates in full color typical plants of 'ScaMav01' grown in a field in Heemskerk, The Netherlands.

Figure 2:
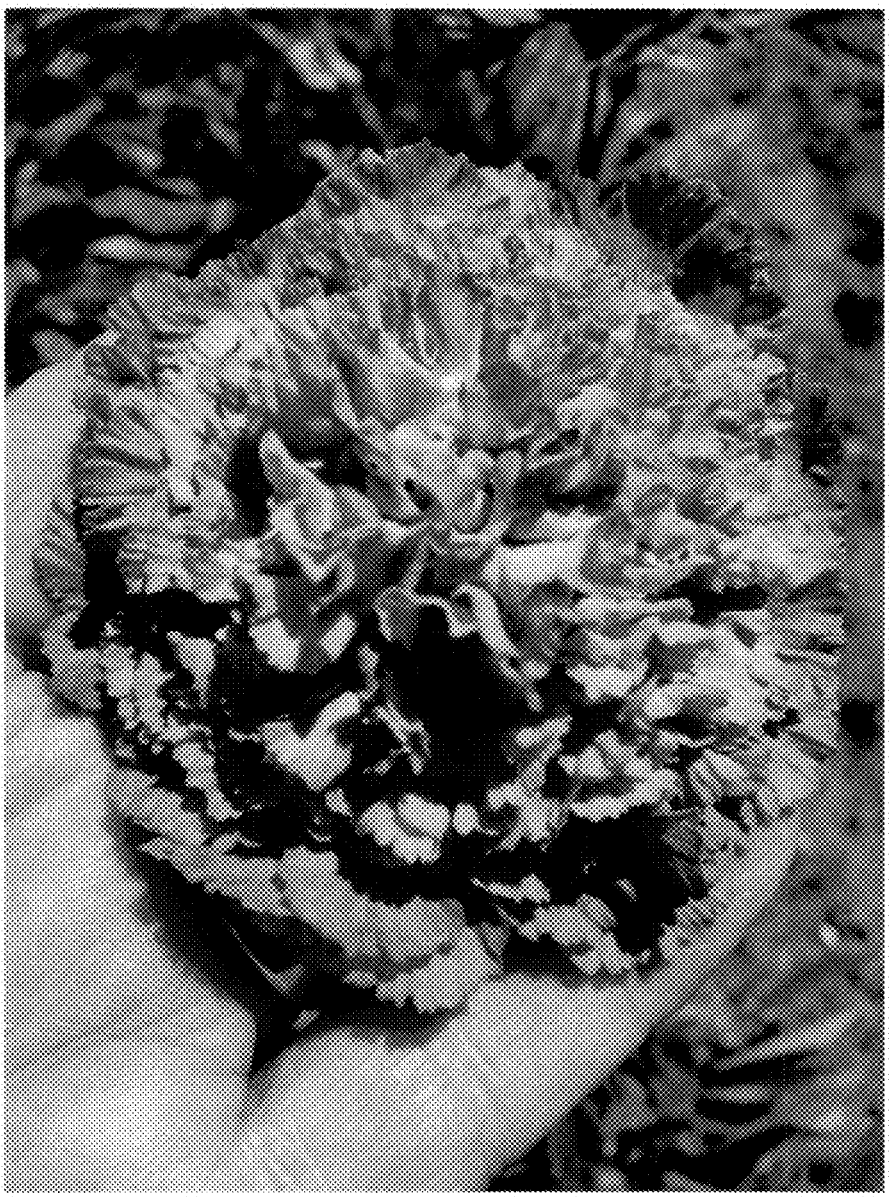

FIG. 2 illustrates in full color a typical inflorescence of 'ScaMav01'.

Photos are of plants of approximately 9 months of age. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'ScaMav01' plants grown in a field in Heemskerk, The Netherlands, under natural lighting. Measurements were taken during August of 2023. The plants were approximately 2 years old. The growing temperature ranged from approximately 12° C. to 35° C. during the days, 4° C. to 20° C. during the nights. Measurements and numerical values represent averages of typical plant types. Botanical classification: *Scabiosa caucasica* 'ScaMav01'.

PROPAGATION

Time to initiate rooting: 6 weeks in spring/summer.
Time to rooted plant: 12 weeks in spring/summer.
Root description: Fine, fibrous.

PLANT

Plant type: Herbaceous perennial.
Growth habit: Upright, clump forming.
Height: 60 to 70 cm. to top of flowers (and approx. 20 cm to top of foliage).
Plant spread: 20 to 35 cm.
Growth rate: Moderate to fast.
Stem:
- *Quantity.*—60 for 1 yr plant; up to 120 for 2 yr plant
- *Diameter.*—3 to 5 mm.
- *Shape.*—Cylindrical.
- *Color.*—RHS Green 143B.
- *Texture.*—Pubescent.
- *Strength.*—very strong.

Internode length: N/A.

FOLIAGE

Leaf:
- *Arrangement.*—Opposite.
- *Attachment.*—Sessile.
- *Length.*—15 to 25 cm.
- *Width.*—2 to 5 cm.
- *Shape.*—Linear.
- *Apex.*—Acute.
- *Base.*—Attenuate.
- *Margin.*—Entire.
- *Texture.*—Slightly pubescent.
- *Color.*—Upper side: RHS Green 141B. Under side: RHS Green 141B.
- *Venation.*—Type: Pinnate. Foliage color uniform throughout and underneath.

FLOWER

Natural flowering season: Spring, Summer, Autumn.
Flower/inflorescence type: Terminal hemispherical heads. Densely packed florets with no significant difference between outer and inner florets.
Quantity of inflorescences per plant: 5 to 8.
Flower arrangement: Asymmetric outer florets with narrow tube expanding into 2 lips—an upper lip with 3 large lobes, and lower lip with 2 or 3 smaller lower lobes.
Persistence: Persistent.
Fragrance: Musky.
Inflorescence:
- *Diameter.*—7 to 8 cm. Depth (height): About 5 to 6 cm.

Bud:
- *Shape.*—Globular.
- *Depth (height).*—1-2 cm.
- *Diameter.*—2-3 cm.
- *Color.*—RHS Yellow-Green 150C in tight bud.

Florets:
- *Quantity.*—80-120 per inflorescence.
- *Length.*—2 to 4 cm.
- *Diameter (width).*—1.5 to 2 cm.
- *Shape.*—Funnelform.
- *Margin.*—Crenulate, undulate.
- *Surface.*—Smooth all surfaces. Color: Outer surface: RHS 91A and 92B. Inner surface: RHS 91C.
- *Tube.*—Length: 1.0-1.5 cm. Diameter: 5 mm. Pubescence: None visible. Color: Outer surface: RHS 91A and 92B. Inner surface: RHS 91C.
- *Sepals.*—Quantity: 10-12. Shape: Linear. Margin: Entire. Apex: Acute. Length: 2 to 3 cm. Width: 4 mm. Color: RHS Green 143A.

Pedicel:
- *Shape.*—Round.
- *Length.*—3 to 5 mm.
- *Diameter.*—1 mm.
- *Texture.*—
- *Color.*—
- *Strength.*—
- *Prickles.*—No.

REPRODUCTIVE ORGANS

Stamens:
- *Number.*—4.
- *Filament length.*—Approximately 4 mm.
- *Filament width.*—Approximately 0.5 mm.
- *Filament color.*—RHS 91D.

Anthers:
- *Length.*—Approximately 1 mm.
- *Width.*—Approximately 0.5 mm.
- *Color.*—Near Yellow-Green RHS 150C.
- *Pollen color.*—Near Yellow-Green RHS 150C.

Pistil: One. About 2 mm long, colored Green-White 159D and having a capitate stigma. Ovary 0.5 to 1 mm.

OTHER CHARACTERISTICS

Seeds and fruits: Fruit/seed vessel produced.
Disease/pest resistance: Neither resistant nor susceptibility to normal diseases and pests of *Scabiosa* has been observed.
Temperature tolerance: Cold hardy to−20° C.

I claim:

1. A new and distinct *Scabiosa* plant named 'ScaMav01', substantially as illustrated and described herein.

* * * * *